(12) United States Patent
Booth et al.

(10) Patent No.: US 6,685,665 B2
(45) Date of Patent: Feb. 3, 2004

(54) CANNULA ASSEMBLY

(75) Inventors: Charles S. Booth, Livonia, MI (US); David McDonough, Ann Arbor, MI (US)

(73) Assignee: Pall Corporation, East Hills, NY (US)

( * ) Notice: Subject to any disclaimer, the term of this patent is extended or adjusted under 35 U.S.C. 154(b) by 19 days.

(21) Appl. No.: 09/948,127

(22) Filed: Sep. 7, 2001

(65) Prior Publication Data

US 2002/0128603 A1 Sep. 12, 2002

Related U.S. Application Data

(60) Provisional application No. 60/231,299, filed on Sep. 8, 2000.

(51) Int. Cl.[7] ............................................. A61M 37/00
(52) U.S. Cl. ......................... 604/26; 604/27; 604/506; 604/158; 604/164.01; 604/164.02; 604/167.01; 604/264; 606/167; 606/185
(58) Field of Search ............................. 604/23–26, 27, 604/30, 33, 35, 43–45, 500, 506, 104, 126, 158, 264, 164.01–164.03, 164.06, 164.09, 164.1, 164.12, 167.01–167.06, 268; 55/385.4, 485, 482, 486; 96/134; 606/167, 191, 185

(56) References Cited

U.S. PATENT DOCUMENTS

| | | | |
|---|---|---|---|
| 3,817,389 A | * 6/1974 | Weichselbaum | 210/448 |
| 3,854,907 A | * 12/1974 | Rising | 96/219 |
| 4,144,040 A | 3/1979 | Claes et al. | |
| 4,246,558 A | * 1/1981 | Zubaty et al. | 335/20 |
| 4,309,992 A | * 1/1982 | Dodak et al. | 604/19 |
| 4,459,139 A | 7/1984 | vonReis et al. | |
| 4,535,773 A | 8/1985 | Yoon | |
| 4,610,683 A | * 9/1986 | Vaillancourt | 604/405 |
| 4,735,603 A | 4/1988 | Goodson et al. | |
| 4,743,243 A | * 5/1988 | Vaillancourt | 604/405 |
| 4,834,108 A | * 5/1989 | Vaillancourt | 600/486 |
| 4,935,006 A | * 6/1990 | Hasson | 604/43 |
| 5,066,288 A | 11/1991 | Deniega et al. | |
| 5,098,375 A | 3/1992 | Baier | |
| 5,098,407 A | 3/1992 | Okamura | |
| 5,199,944 A | 4/1993 | Cosmescu | |
| 5,246,419 A | 9/1993 | Absten | |
| 5,290,237 A | 3/1994 | Verkaart | |
| 5,290,246 A | * 3/1994 | Yamamoto et al. | 604/167.03 |
| 5,300,084 A | 4/1994 | Johnson | |
| 5,334,163 A | * 8/1994 | Sinnett | 604/236 |
| 5,336,170 A | * 8/1994 | Salerno et al. | 604/24 |
| 5,360,396 A | 11/1994 | Chan | |
| 5,411,474 A | 5/1995 | Ott et al. | |
| 5,417,655 A | * 5/1995 | Divilio et al. | 604/22 |
| 5,499,970 A | 3/1996 | Olson | |
| 5,514,087 A | * 5/1996 | Jones | 604/26 |
| 5,540,587 A | 7/1996 | Malmin | |
| 5,578,000 A | 11/1996 | Greff et al. | |
| 5,582,165 A | * 12/1996 | Bryan et al. | 128/207.14 |
| 5,688,256 A | * 11/1997 | Surratt et al. | 604/355 |
| 5,709,675 A | * 1/1998 | Williams | 606/1 |
| 5,716,343 A | 2/1998 | Kriesel et al. | |
| 5,722,962 A | 3/1998 | Garcia | |
| 5,779,662 A | * 7/1998 | Berman | 604/22 |
| 5,902,264 A | 5/1999 | Toso et al. | |
| 5,941,852 A | 8/1999 | Dunlap et al. | |
| 5,947,932 A | 9/1999 | Desecki et al. | |
| 5,980,492 A | * 11/1999 | Rosen et al. | 604/168.01 |
| 6,001,077 A | 12/1999 | Ellman et al. | |
| 6,051,015 A | 4/2000 | Maahs | |
| 6,110,259 A | * 8/2000 | Schultz et al. | 95/273 |
| 6,206,878 B1 | * 3/2001 | Bishop et al. | 606/49 |
| 6,221,050 B1 | * 4/2001 | Ishida | 604/167.03 |

FOREIGN PATENT DOCUMENTS

WO      WO 99/31954      7/1999

\* cited by examiner

Primary Examiner—Brian L. Casler
Assistant Examiner—Cris L. Rodriguez
(74) Attorney, Agent, or Firm—Leydig, Voit & Mayer, Ltd.

(57) ABSTRACT

Cannulas, as well as cannula assemblies including gas filters, are disclosed.

27 Claims, 11 Drawing Sheets

CANNULA ASSEMBLY

This application claims the benefit of U.S. provisional patent application No. 60/231,299, filed Sep. 8, 2000, which is incorporated by reference.

TECHNICAL FIELD

This invention relates to cannulas and cannula assemblies for use with surgical instruments and/or for use in filtering gas.

BACKGROUND OF THE INVENTION

During some medical procedures, e.g., laparoscopic and endoscopic surgery, a suitable gas is introduced into the abdominal cavity to inflate the abdomen, and this introduction of gas is commonly referred to as insufflation. The inflation of the abdomen separates the interior organs and provides an enlarged cavity within which to perform the surgery. Typically, one or more trocars (slidably disposed in a cannula or cannula sleeve) are used to puncture the abdomen, the trocar is withdrawn, and insufflation gas is passed through at least one of the cannula(s) to inflate the abdomen. One or more instruments involved in the procedure, e.g., a laparoscope, scalpel, laser, ultrasonic device (such as an ultrasonic tissue fragmentation device) and/or electrocautery device, can be inserted through the appropriate cannula(s) as needed.

Lasers, ultrasonic tissue fragmentation devices, and electrocautery devices are typically used for cutting of tissues and/or blood vessels. However, this cutting often produces "smoke" (e.g., vapor and/or mist) that can cloud or obstruct the surgeon's view of the operative site. During the surgical procedure, gas can be vented from the abdominal cavity and into the surrounding atmosphere through a port on the cannula, e.g., to clear the surgeon's field of vision of smoke generated by the cutting instruments. The gas can be released multiple times (typically intermittently, upon opening and closing a valve on the port) during the procedure. Once surgery is completed, the gas used to inflate the cavity is vented from the abdominal cavity, and this release of gas (and associated smoke) is referred to as de-sufflation (or exofflation).

Smoke can contain toxic, odiferous, and otherwise undesirable material that, if released into the environment of the operating room, could expose the surgeon and the surgeon's staff to a health risk. Additionally, the gas to be introduced into the abdominal cavity can include undesirable material such as particulate and/or microbial contaminants.

Attempts have been made to filter gas passed from or into the abdominal cavity of the patient using a filter attached to a fitting on the cannula. However, these device arrangements (i.e., an external filter attached to a cannula fitting) have suffered from a number of drawbacks. For example, some of these device arrangements are bulky and/or heavy, and can interfere with the ability to move in and around the surgical site. The combined weight of the cannula and filter can put strain on the incision and/or cause leakage of gas. The filters may become plugged, fail to remove sufficient undesirable material and/or may require a labor intensive effort (possibly requiring numerous steps) to attach and operate them. Special equipment (e.g., evacuators) may have to be utilized with the filters.

The present invention provides for ameliorating at least some of the disadvantages of the prior art. These and other advantages of the present invention will be apparent from the description as set forth below.

SUMMARY OF THE INVENTION

In accordance with an embodiment of the instant invention, a cannula assembly is provided comprising a housing having at least a first port and a second port, and defining a fluid flow path between the two ports, and a gas filter disposed in the housing, across the fluid flow path. Preferably, the housing includes a cannula sleeve wherein the sleeve comprises the second port, and the housing is arranged to allow a trocar and/or at least one surgical instrument to be removably passed through the second port. In accordance with the invention, the filter is adapted to filter gas passed from the first port to the second port and/or gas passed from the second port to the first port. Accordingly, the cannula assembly is suitable for use during insufflation and/or de-sufflation. If desired, different embodiments of the cannula assembly can be used for insufflation and de-sufflation.

In some embodiments, the housing is re-usable and the gas filter can be removed from within the housing and discarded, and a replacement filter can be inserted therein.

In another embodiment, a cannula is provided, comprising a housing comprising having a first port and a second port, and defining a fluid flow path between the first port and the second port, the housing further comprising a first portion attached to a second portion, the first portion having a larger inner diameter than the second portion, the second portion comprising a cannula sleeve, the sleeve having a first end proximal to the first portion, and a second end distal to the first portion, the second end comprising the second port, wherein the sleeve includes additional openings (e.g., two or more openings) between the first end and the second end, and the cannula also defines a fluid flow path between the first port and the additional openings. In an embodiment, the cannula includes a gas filter to provide a cannula assembly.

Methods for using the cannula assemblies and cannulas, and systems comprising the cannula assemblies and cannulas, are also provided.

In preferred embodiments of de-sufflation applications, the gas filter removes laparoscopic smoke and reduces odor as the gas passes through the cannula assembly to the exterior of the housing.

Embodiments of the cannula and cannula assembly are suitable for use at any desirable constant or variable gas flow rate, and de-sufflation can be carried out without attaching a vacuum system to the assembly. Preferably, the cannula assembly can be easily added to any suitable system (e.g., a system for use in laparoscopic surgery). In an embodiment, the assembly (that can be part of a system) allows one-handed gas flow adjustment.

Embodiments of the invention are particularly for use in surgical environments, especially for use in laparoscopic surgery, as they can allow the surgical procedure to be completed more quickly and/or cost efficiently, e.g., by reducing the amount of valuable surgeon-, nurse-, technician- and/or operating room-time needed for the procedure. Time savings are particularly advantageous, since, for example, as of 1999, studies have estimated the value of time in the operating room during laparoscopic surgery as in the range of from $20 per minute to $120 per minute, or more.

The following definitions are used in accordance with the invention.

Trocar. A trocar (sometimes referred to as a stylet or obdurator) comprises a pointed instrument, preferably for puncturing the wall of a body cavity.

Cannula. A cannula comprises a sleeve (tube) for insertion into a body cavity. The sleeve has a lumen, and during insertion, the lumen is typically occupied by a trocar. Typically, fluid (e.g., at least one gas) is passed through the cannula into and/or from the cavity after the trocar is removed from at least a portion of the lumen. The trocar can be removed from the cannula, and one or more other surgical instruments can be passed through the cannula and into the body cavity. In some embodiments, gas is passed through the cannula while a surgical instrument (e.g., other than a trocar) is in the cannula.

Cannula Assembly. A cannula assembly comprises a housing comprising a cannula, the housing having at least a first port and a second port, and defining a fluid flow path between the two ports, and at least one gas filter disposed in the housing, across the fluid flow path. Preferably, the housing includes a cannula sleeve wherein the sleeve comprises the second port, wherein at least a portion of the housing has an interior diameter and/or volume that is greater than the interior diameter and/or volume of the cannula sleeve. For example, the housing can include a larger portion suitable for containing one or more gas filters therein, wherein the housing is integrally attached to a narrower portion comprising the cannula sleeve. Typically, the larger portion includes a plurality of side walls (e.g., two sets of opposing walls) or a continuous side wall. The housing can include a top and/or bottom wall, and any of the walls can be in the form of a hinged and/or removable cover. Preferably, the larger portion of the housing includes at least one wall comprising the first port. The ports can include a plurality of openings (e.g., formed by a grid or a series of slits or perforations). In an embodiment, the cannula assembly includes a trocar, e.g., a cannula assembly includes a trocar equipped with a cannula.

The cannula assembly can include additional elements such as, but not limited to, at least one of a handle, one or more valves, one or more additional ports (e.g., a third port, and in some embodiments, at least a fourth port, and at least one of these ports can include a plurality of openings), one or more interior walls, one or more connectors, and at least one instrument sealing arrangement. Preferably, the cannula assembly includes at least one instrument sealing arrangement (e.g., comprising at least one of a gasket, seal, and valve such as a duckbill valve), that can be pliable, adapted to contact the instrument(s) used during the procedure and reduce or minimize the leakage of gas from the inflated body cavity.

In a preferred embodiment, the housing is arranged to allow a surgical instrument (such as, for example, at least one of a trocar, laparoscope, optic probe, scalpel, laser, ultrasonic device, electrocautery device, and camera) to be removably passed through the second port.

Gas Filter. A gas filter (preferably a smoke filter) comprises at least one gas filter element (preferably a smoke filter element) comprising a porous retentive element, i.e., at least one porous medium that retains at least one undesirable material such as at least one of microorganisms (e.g., bacteria), viruses, cells, body fluids, particulates, aerosols and liquid droplets, and allows at least a portion of the gas to pass through the retentive element, wherein the gas is depleted of at least some level of the undesirable material(s) as the gas passes through the filter. The retentive element can also retain or reduce the passage therethrough of other undesirable material such as at least one of benzene, hydrogen cyanide, formaldehyde, and toluene, and/or the element can reduce the passage of odor therethrough. The porous retentive element comprising at least one porous medium can comprise a fibrous web, a membrane, combinations thereof, a composite, and the like.

The gas filter element (and the porous medium) can have any suitable physical dimensions and typically will be in sheet, cylindrical and/or pleated form having opposing sides (e.g., a first side and an opposing second side, in relation to a fluid to be treated wherein at least a portion of the gas is passed through the element) with a central portion therebetween, wherein the pores in the porous medium will generally enable fluid communication between the two opposing sides (e.g., between the first and second sides) of the element. Typically, the gas filter element comprises at least one hydrophobic membrane (preferably a hydrophobic microporous membrane) and/or at least one hydrophobic fibrous medium, through which the fluid (e.g., gas) to be treated passes.

The gas filter can have any suitable pore structure, for example, a Dioctyl Phthalate (DOP) smoke penetration rating (for example, measuring the membrane efficiency by the Monodisperse DOP Smoke Test, e.g., as described in ASTM D 2986-95a), a pore size (for example, as evidenced by bubble point, or by $K_L$ as described in, for example, U.S. Pat. No. 4,340,479), a pore rating, or a pore diameter (e.g., when characterized using the modified OSU F2 test as described in, for example, U.S. Pat. No. 4,925,572). The gas filter can have a pore structure that is uniform, substantially uniform, or it can vary in a continuous, a discontinuous, or a stepwise manner. For example, a smoke filter can have a graded pore structure. In some embodiments, a gas filter includes a plurality of elements and/or layers wherein individual elements and/or layers have different pore structures, e.g., different pore ratings. For example, a gas filter can comprise a gas filter element having a plurality of layers wherein at least two layers have different pore ratings.

The gas filter (preferably, the smoke filter) can include additional elements, layers, or structures, which can also be membranes, or other porous media. For example, in some embodiments, the smoke filter can include additional components that have different structures and/or functions, e.g., at least one of prefiltration, odor-reduction, support, drainage, spacing and cushioning. The gas filter can also include, for example, at least one of an endcap, a core, and a frame.

In those embodiments wherein the cannula assembly includes a plurality of gas filters, e.g., one filter for insufflation gas, and another filter for de-sufflation gas, the filters can have different configurations (e.g., pore structures, effective filtration areas and/or different elements).

Smoke. As used herein, the term "smoke" includes gas (e.g., the insufflation gas in the abdominal cavity, such as, for example, $CO_2$), as well as some of the material and/or some of the by-products produced by the ablation of tissues and/or blood vessels (e.g., mist, aerosols and droplets). Smoke can include additional material, such as toxic, odiferous, and otherwise undesirable material (e.g., benzene, hydrogen cyanide, toluene, formaldehyde, carbon monoxide, viruses, bacteria, cells, and/or body fluids from diseased tissue of the patient). In some embodiments, smoke includes at least one of bacteria and viruses.

BRIEF DESCRIPTION OF THE DRAWINGS

FIG. 6 shows several views of another embodiment of a cannula assembly including two planar gas filters for de-sufflation gas, and a planar gas filter for insufflation gas, wherein the cannula assembly provides a first fluid flow path through one de-sufflation gas filter, and a second fluid flow path through the other de-sufflation gas filter, and a third fluid flow path through the insufflation gas filter.

SPECIFIC DESCRIPTION OF THE INVENTION

Figure 1:
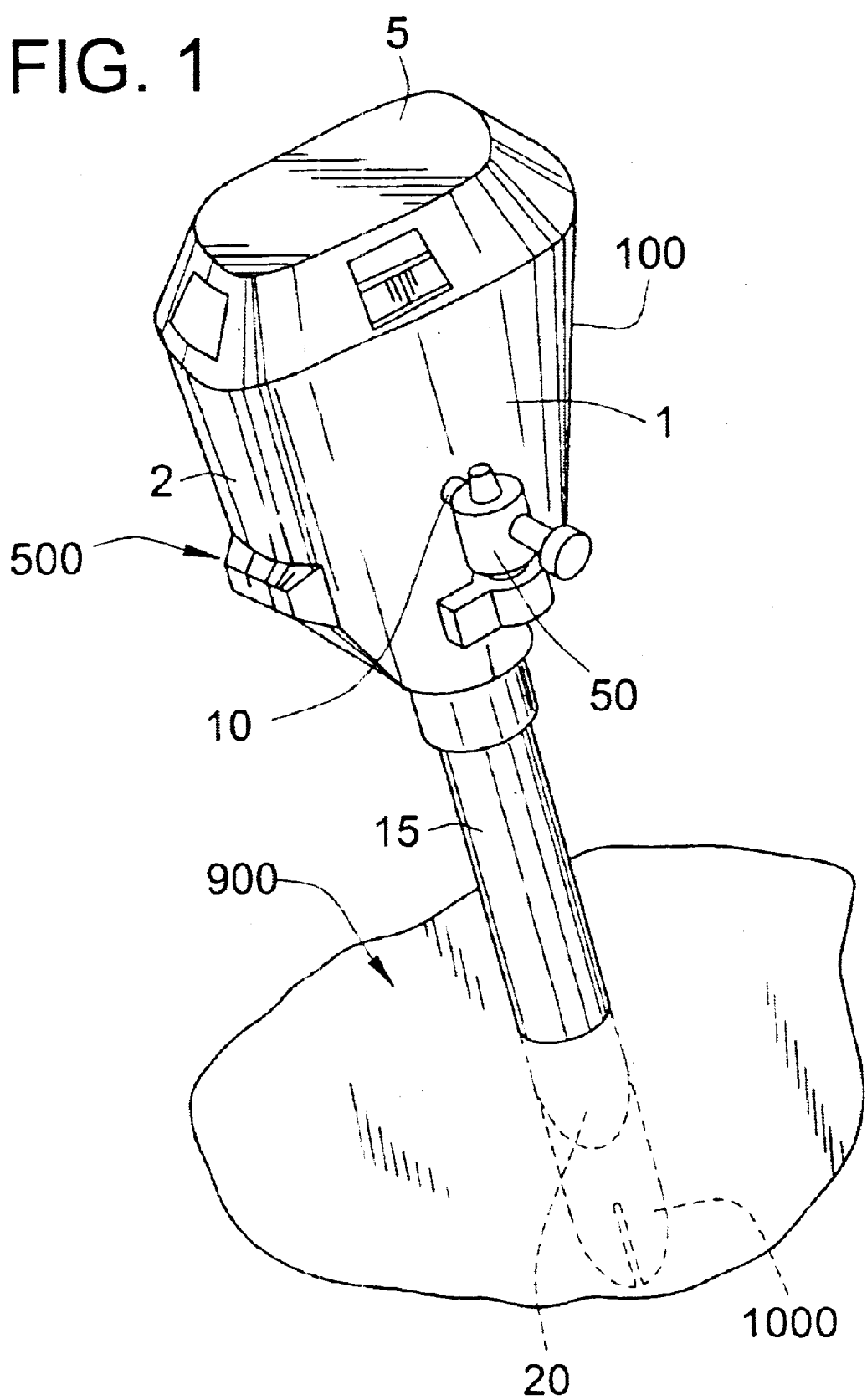
FIG. 1 is an oblique view of an embodiment of a cannula assembly according to the invention (gas filter not shown) also showing a trocar 1000 extending from the cannula sleeve of the cannula assembly, wherein the trocar and the portion of the cannula sleeve extending into the body cavity (the body cavity having a wall 900) are shown in dotted lines.

A cannula assembly according an embodiment of the invention comprises a housing having at least a first port and a second port, and defining a fluid flow path between the two ports, and a gas filter disposed in the housing, across the fluid flow path.

In accordance with an embodiment of the invention, a cannula assembly is provided comprising a housing having at least a first port and a second port, the housing comprising a sleeve wherein the sleeve comprises the second port, wherein said housing defines a fluid flow path between the first port and the second port, and a gas filter disposed in the housing, across the fluid flow path, wherein said gas filter comprises at least one gas filter element comprising at least one porous medium.

A cannula assembly according to another embodiment of the invention comprises a housing having at least a first port and a cannula sleeve, the cannula sleeve comprising a second port, wherein said housing defines a fluid flow path between the first port and the second port, and said housing is arranged to allow a surgical instrument to be removably passed through the second port, and a gas filter disposed in the housing, across the fluid flow path, wherein said gas filter comprises at least one gas filter element comprising at least one porous medium.

In some embodiments of the cannula assembly, the gas filter has an opening allowing instrument passage therethrough.

In another embodiment, a cannula is provided comprising a housing comprising having a first port and a second port, and defining a fluid flow path between the first port and the second port, the housing further comprising a first portion attached to a second portion, the first portion having a larger inner diameter than the second portion, the second portion comprising a cannula sleeve, the sleeve having a first end proximal to the first portion, and a second end distal to the first portion, the second end comprising the second port, wherein the sleeve includes two or more openings between the first end and the second end, and the cannula also defines a fluid flow path between the first port and the additional openings.

Embodiments of systems according to the invention comprise at least one conduit in fluid communication with the cannula assembly or cannula. For example, one embodiment of a system comprises a cannula assembly comprising a housing having at least a first port and a second port, and defining a fluid flow path between the two ports, and a gas filter disposed in the housing, across the fluid flow path; and at least one conduit in fluid communication with the first port.

An embodiment of a method for treating at least one gas according to the invention comprises passing a gas through a first port of a housing, through a gas filter in the housing to provide a filtered gas, and passing the filtered gas through a second port of the housing and into a patient's abdominal cavity. In another embodiment, a method for treating gas comprises passing a gas from a patient's abdominal cavity, through a second port of a housing, through a gas filter in the housing to provide a filtered gas, and passing the filtered gas through a first port of the housing. Some embodiments of the method comprise passing a first filtered gas into the patient's abdominal cavity, and passing a second gas from the patient's abdominal cavity and through the filter to provide a second filtered gas, and passing the second filtered gas to the exterior of the housing.

Each of the components of the invention will now be described in more detail below, wherein like components have like reference numbers.

Figure 10:
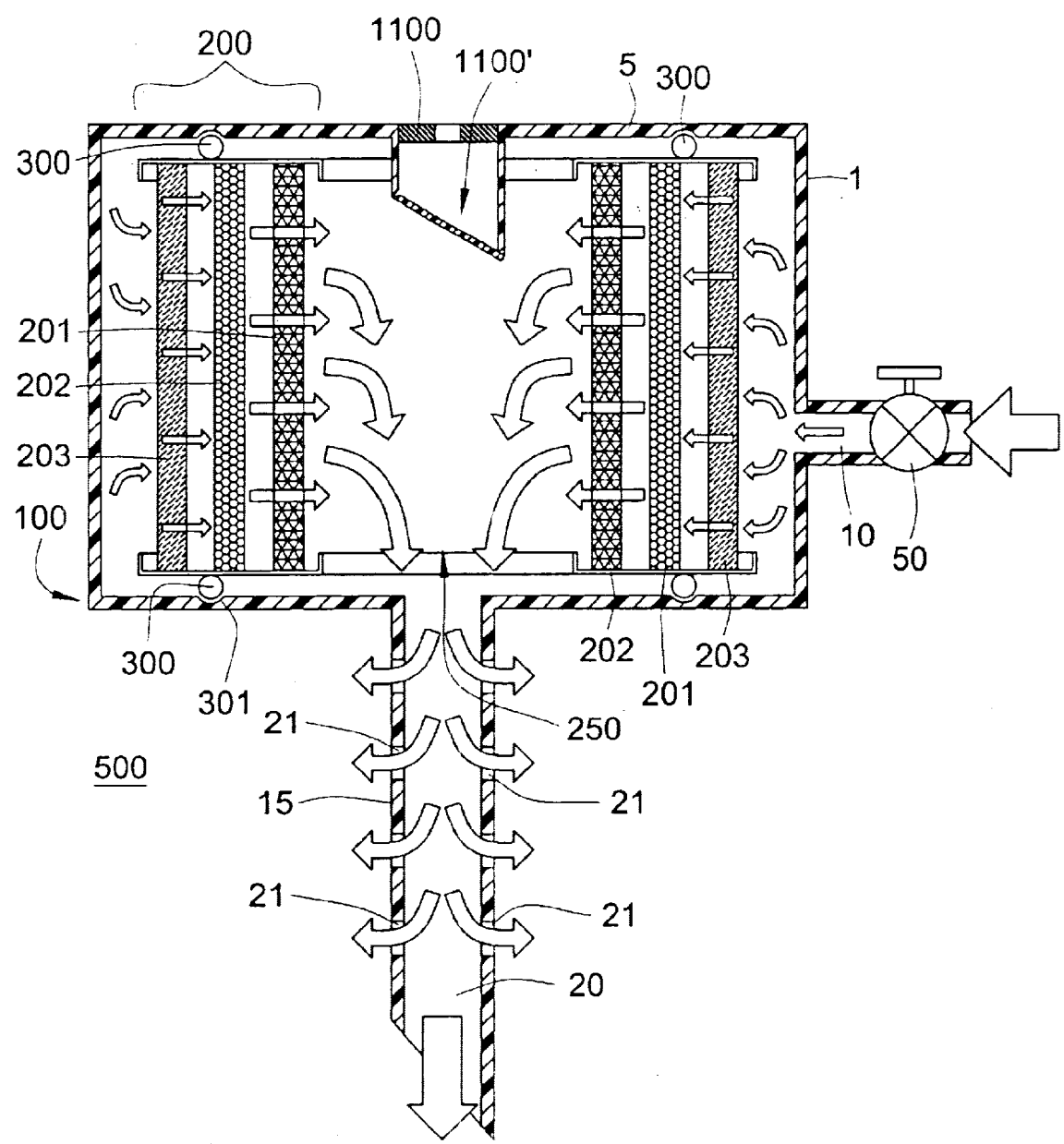
FIG. 10 is a cross-sectional view of another embodiment of a cannula assembly of the present invention including a cannula sleeve having a plurality of openings along a portion of the length of the sleeve, wherein the assembly also includes a cylindrical gas filter arranged to filter insufflation gas.
Figure 11:
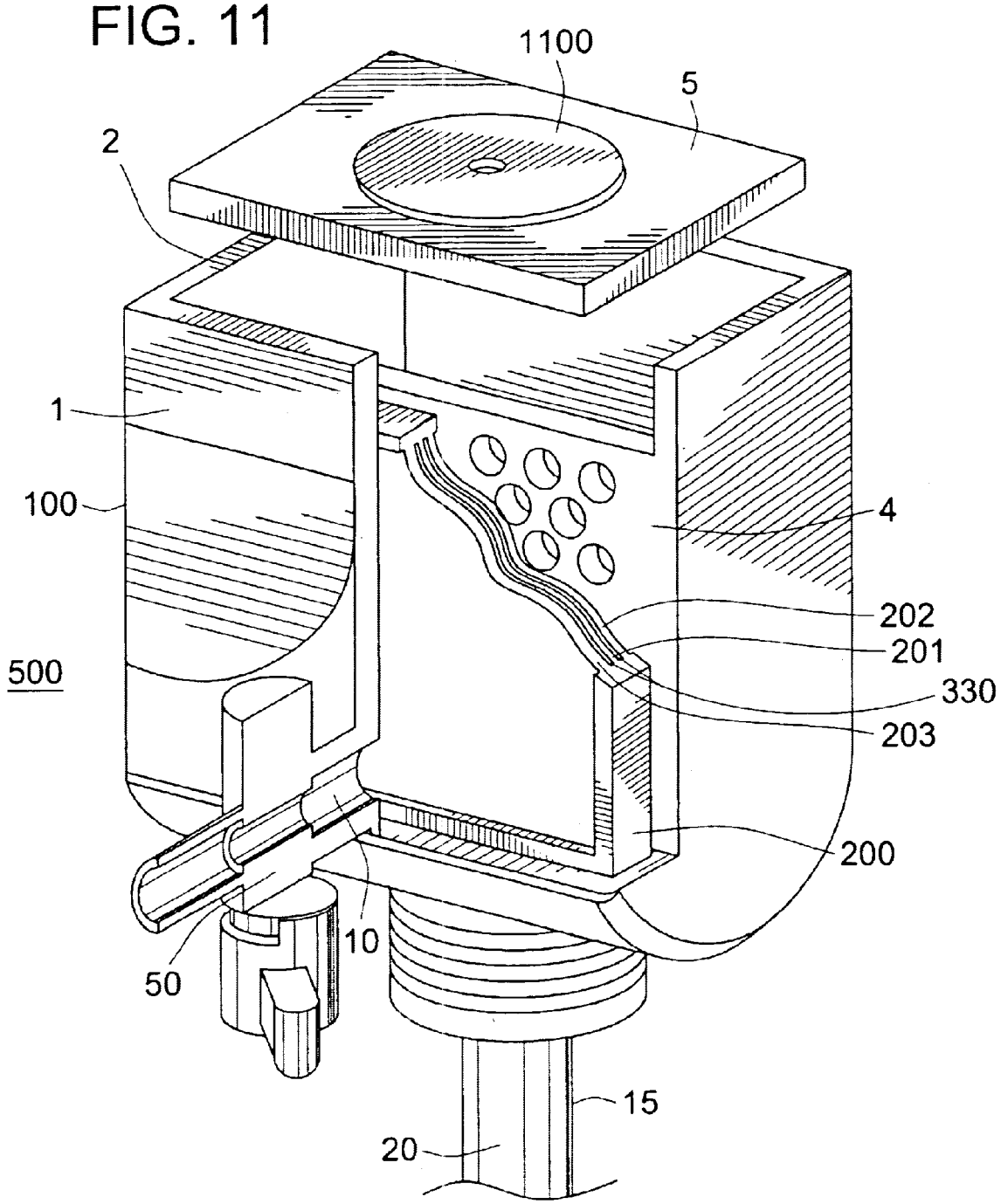
FIGS. 11–13 show oblique, partially exploded views of embodiments of cannula assemblies according to the invention. The cannula assemblies shown in FIGS. 11 and 12 include planar gas filters, and the cannula assembly shown in FIG. 13 includes a cylindrical gas filter.
Figure 12:
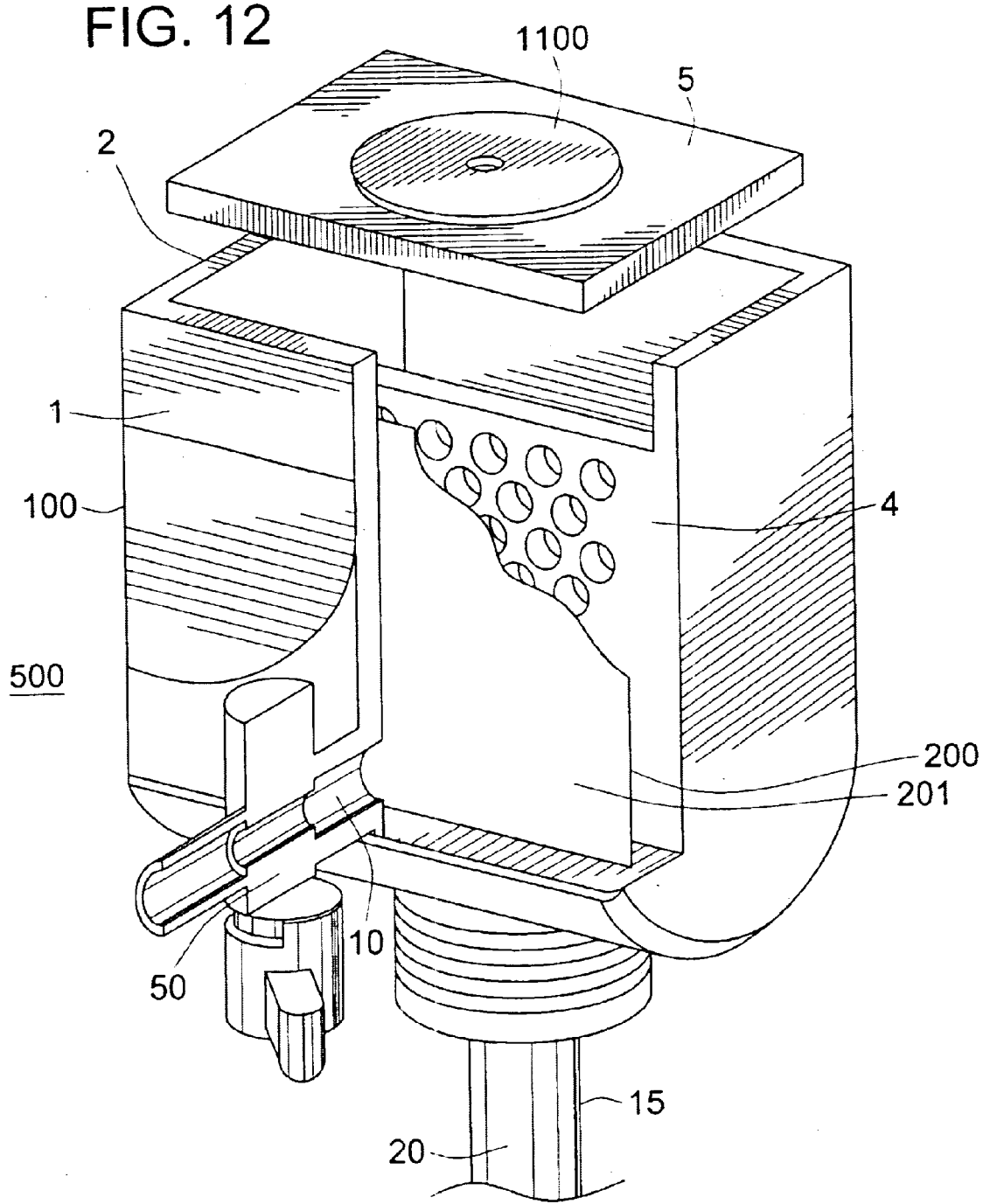
Figure 13:
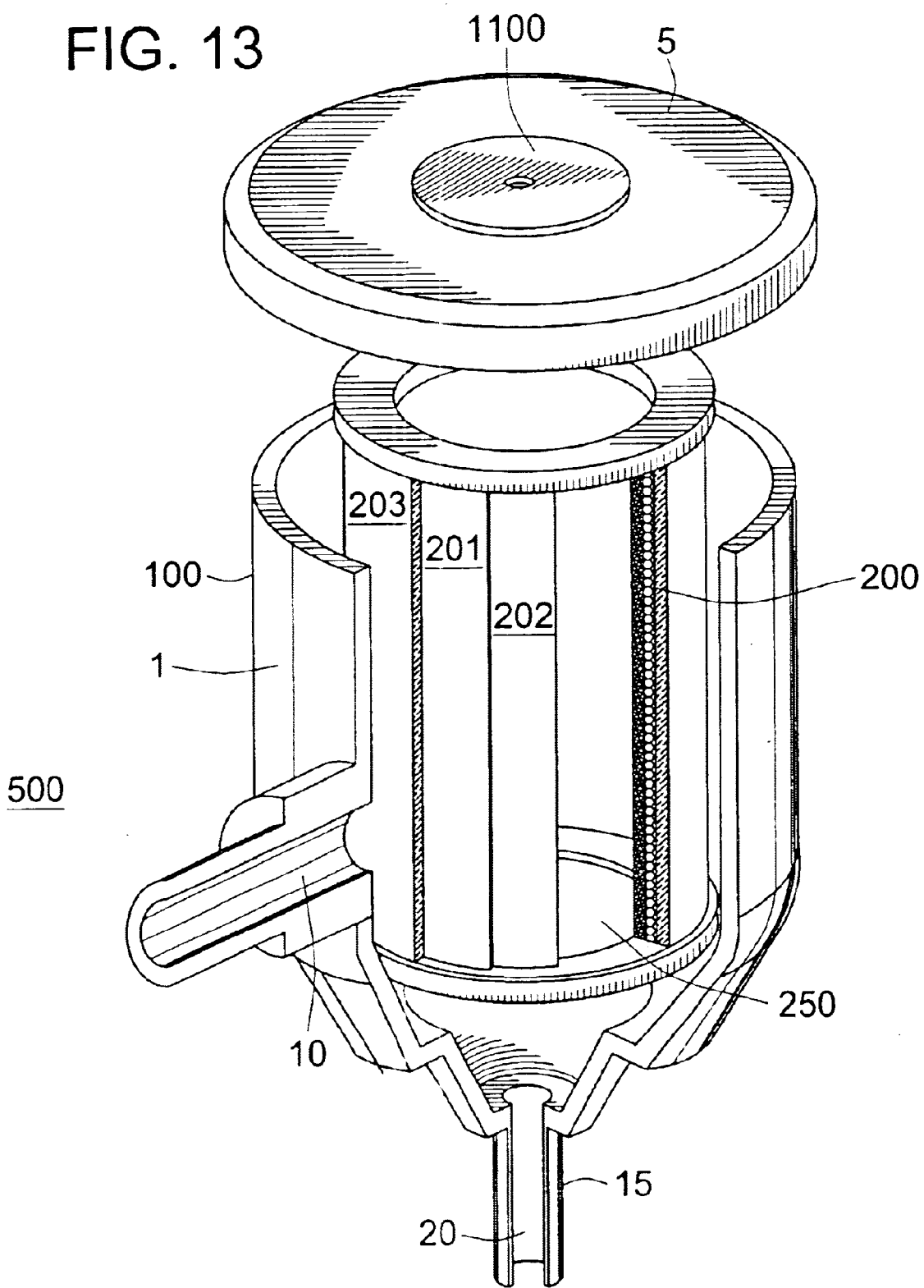

In accordance with some of the illustrated embodiments (e.g., FIGS. 11–13 (oblique, partially exploded views) and FIGS. 2, 5, 6, and 10 (cross-sectional views)), a cannula assembly 500 comprises a housing 100 including at least a first port 10 and cannula sleeve 15 including a second port 20, and defining a fluid flow path between the first port and the second port, and at least one gas filter 200 comprising at least one gas filter element, more preferably a hydrophobic retentive element 201 comprising at least one porous medium, disposed within the walls of the housing and across the fluid flow path. Depending on the application, the fluid flow can be from either port to the other port, or the flow can alternate from one direction to another at different times during a treatment protocol.

Figure 3:
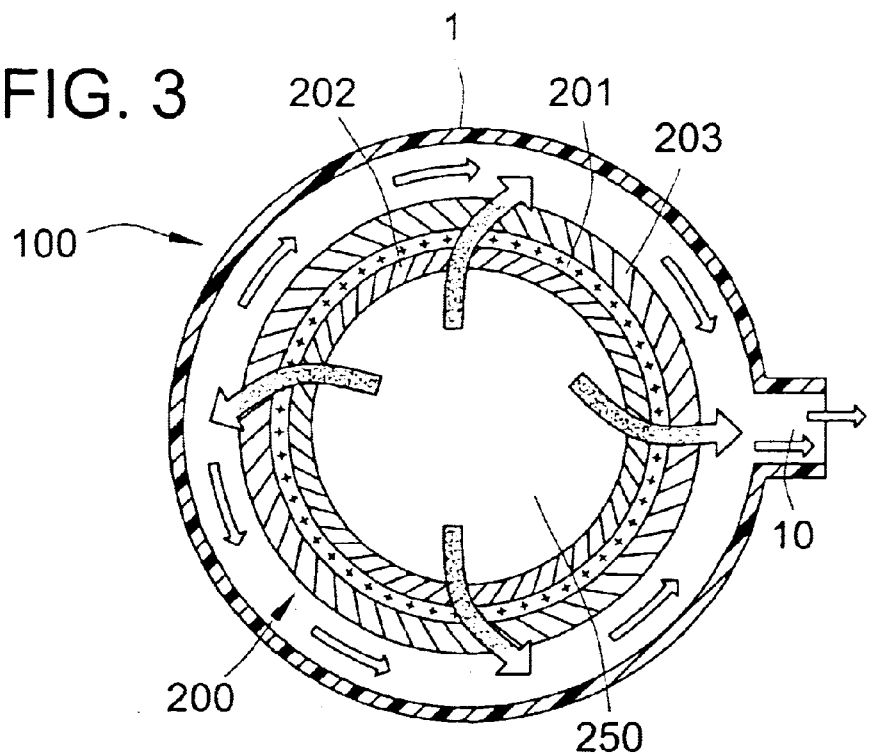
FIG. 3 is a top cross-sectional view of the embodiment illustrated in FIG. 2 along line 3—3.
Figure 4:
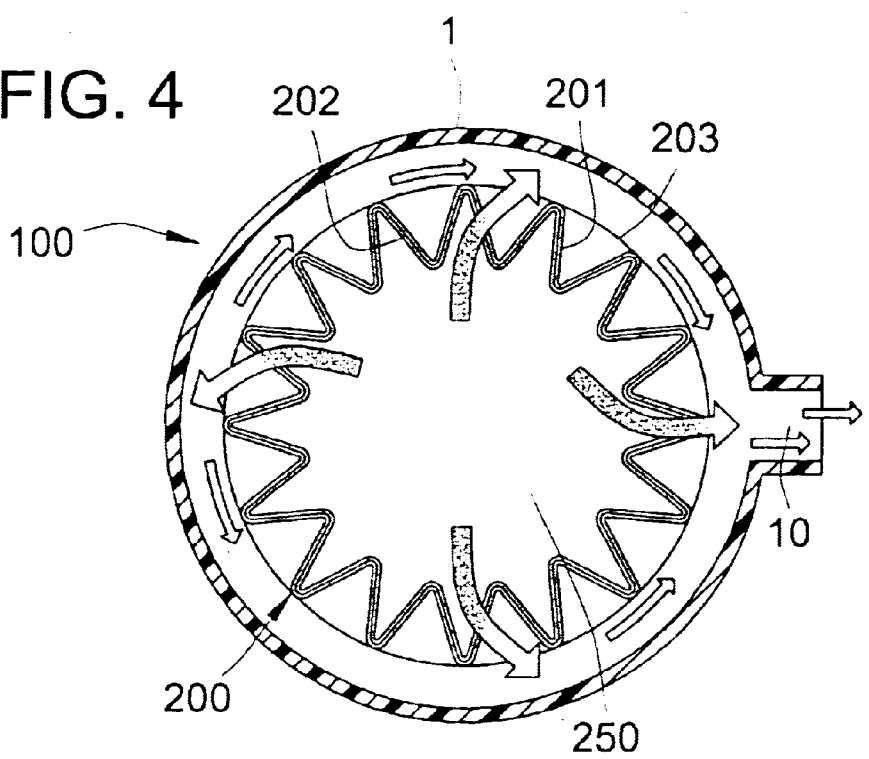
FIG. 4 is a top cross-sectional view of an embodiment of a cannula assembly including a gas filter having a pleated gas filter element.
Figure 5:
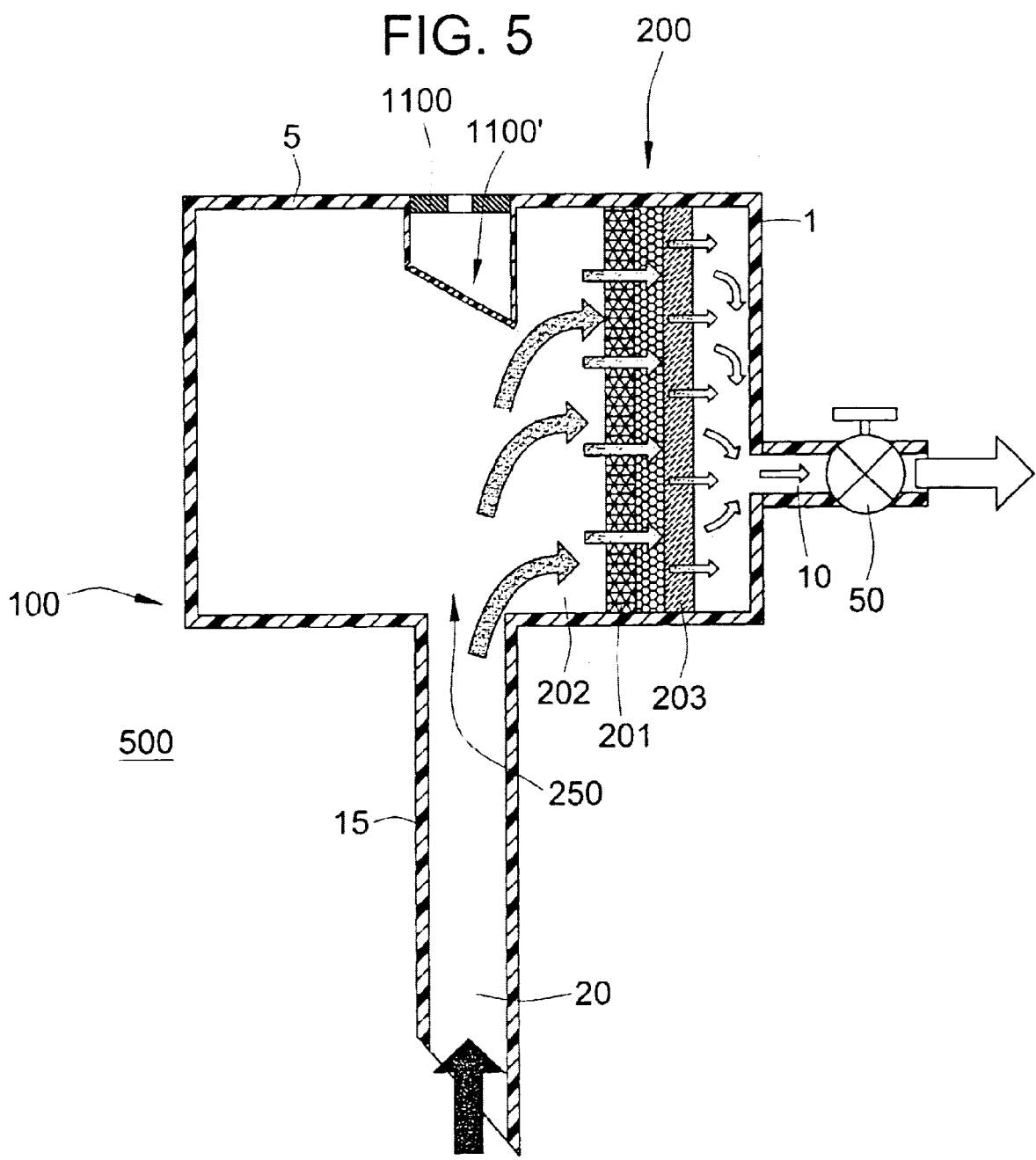
FIG. 5 is another embodiment of a cannula assembly including a planar gas filter.

Typically, as shown in FIG. 1 (showing an oblique view of an embodiment of a cannula assembly 500), the housing 100 includes at least one side wall 1 wherein a portion of the side wall comprises at least the first port 10, and the assembly can include a connector and/or a flow control device 50 such as a valve in fluid communication with the first port. In other embodiments, e.g., as shown in FIGS. 3 (cross-sectional view) and 13 (oblique, partially exploded view), the housing includes a continuous side wall 1 wherein a portion of the side wall comprises at least the first port 10. The housing can include at least one additional wall, e.g., an additional side wall 2 and a top wall 5 as shown in FIG. 1 (other walls not shown in FIG. 1). In some embodiments (not shown) other sections of the housing comprise the first port. For example, the top or bottom wall can comprise the first port.

Figure 6A:
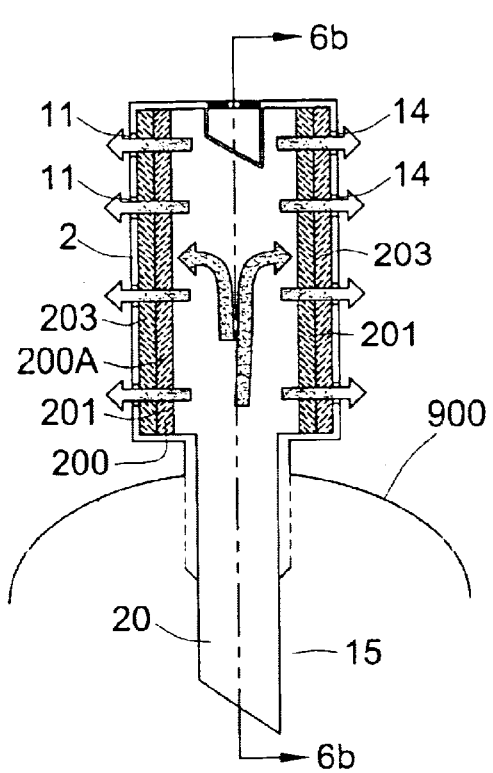
FIG. 6A shows a rear partial cross-sectional view, and also shows the de-sufflation gas flow paths.
Figure 6B:
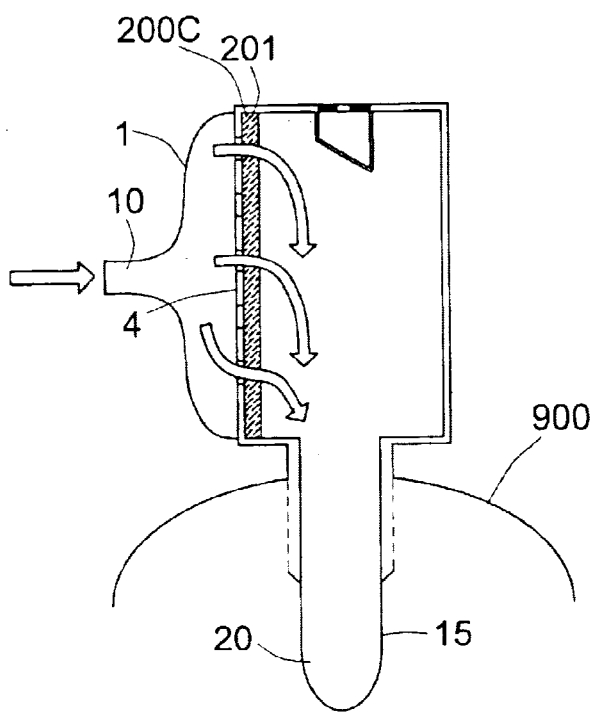
FIG. 6B shows a side partial cross-sectional view, and also shows the insufflation gas flow path.
Figure 6C:
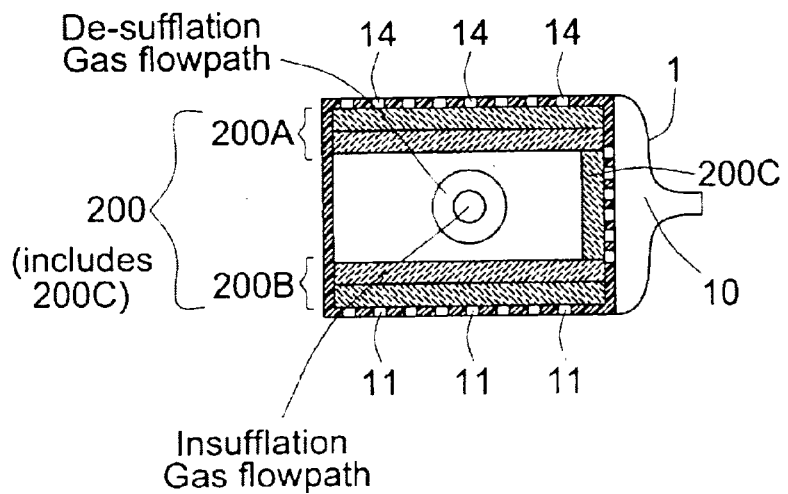
FIG. 6C shows a top cross-sectional view, and also shows the de-sufflation and insufflation gas flow paths.
Figure 8:
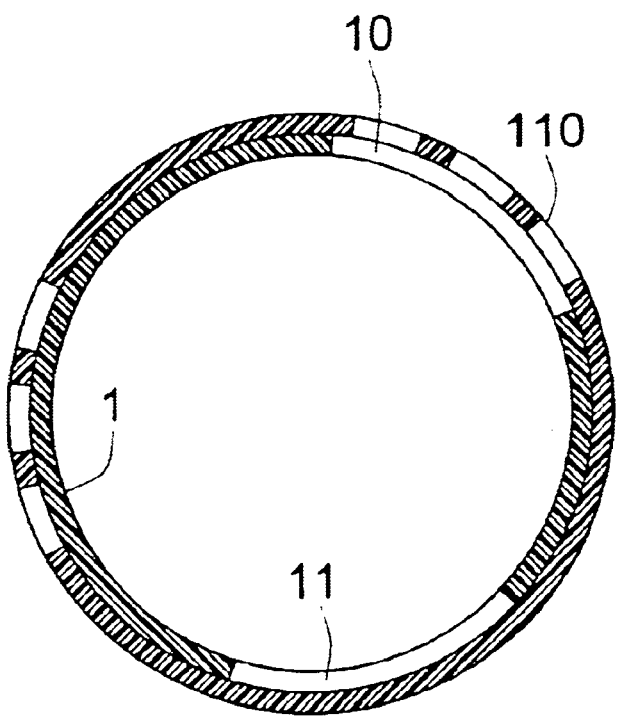
FIG. 8 is a top partial cross-sectional view of an embodiment of a cannula assembly housing wherein the housing has a cylindrical configuration for at least a portion of the side wall, the portion including two ports, and the housing includes a movable cover associated with the ports.

In some embodiments, e.g., as shown in FIGS. 6A, 6C and 8, the cannula assembly includes at least a third port 11, wherein the housing also defines a fluid flow path between the second port and the third port (FIGS. 6B and 8 also show first port 10). FIGS. 6A and 6C show a cannula assembly further comprising a fourth port 14, wherein the housing also defines a fluid flow path between the second port and the fourth port.

Figure 9:
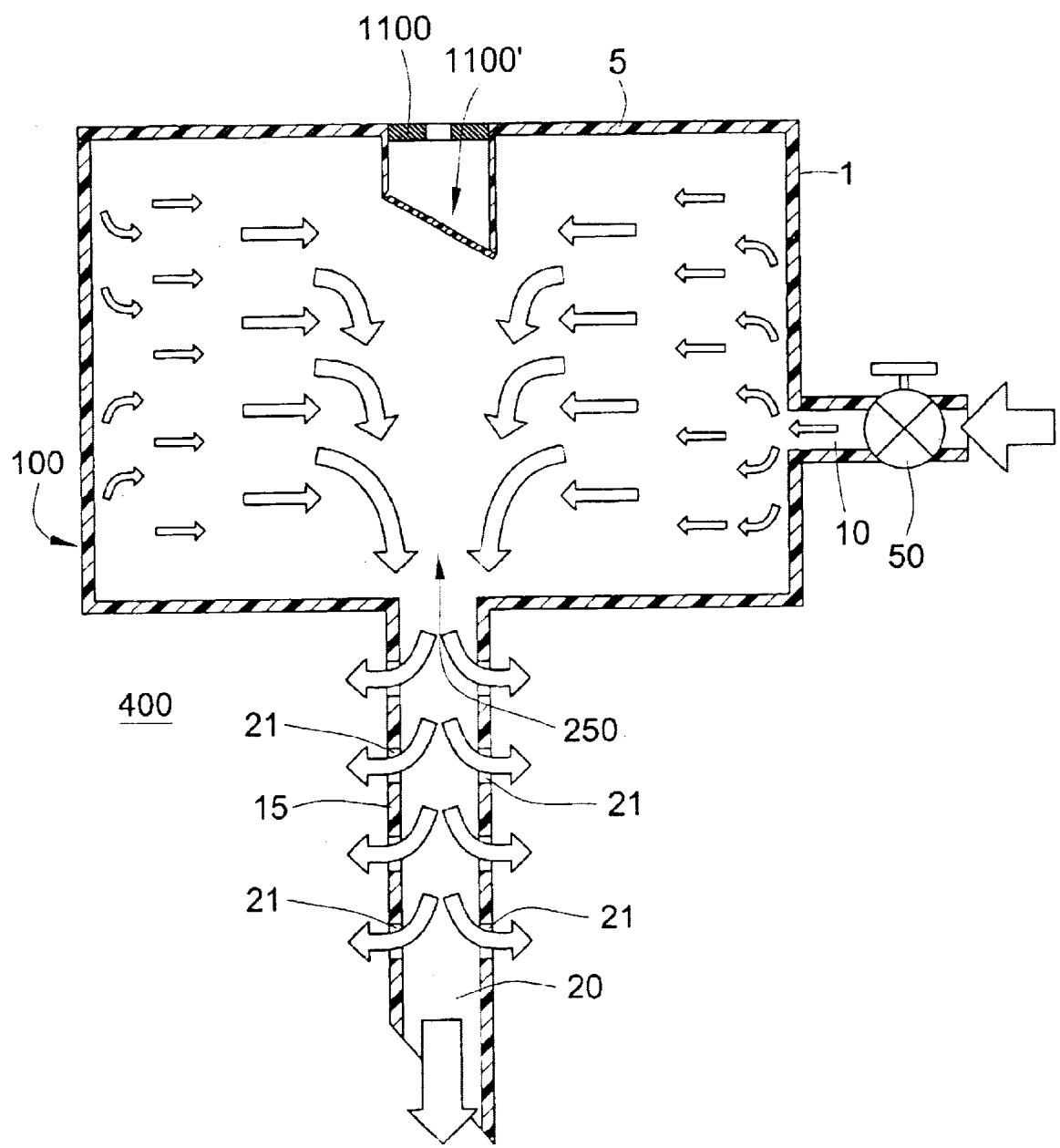
FIG. 9 is a cross-sectional view of an embodiment of a cannula of the present invention including a cannula sleeve having a plurality of openings along a portion of the length of the sleeve.

The illustrated embodiment of a cannula 400 shown in FIG. 9 includes a housing 100, and a flow control device 50 as generally described above, without including a gas filter.

Figure 7:
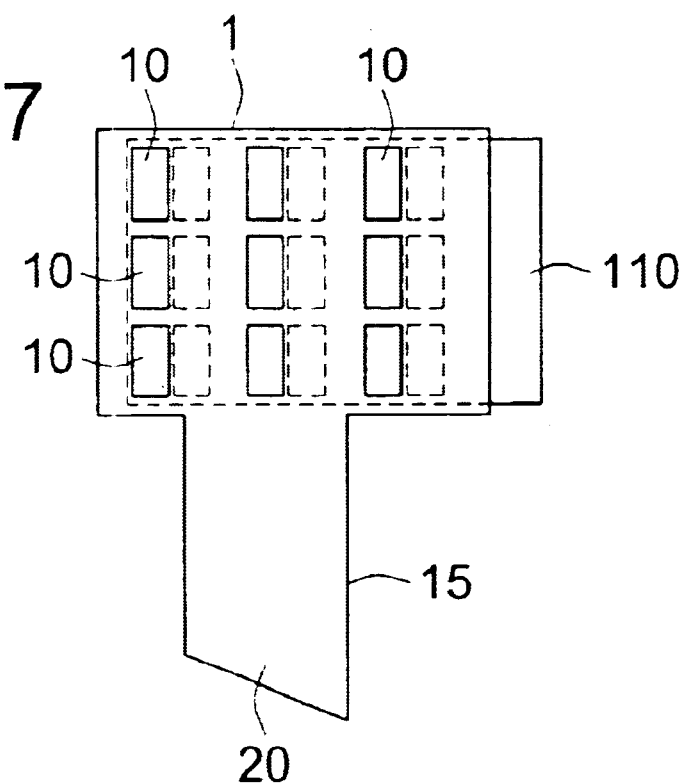
FIG. 7 is an external side view of an embodiment of a cannula assembly wherein the housing has at least one substantially planar wall including a port, and the housing includes a movable cover associated with the port.

In accordance with embodiments of the invention, a port can include a plurality of openings, e.g., as shown in FIGS. 6A, and 7, and the cannula sleeve can include a plurality of openings 21 (e.g., two or more openings, preferably, three or more openings, more preferably, four or more openings, between the proximal end of the sleeve connected to the enlarged portion of the housing, and the distal end of the sleeve away from the enlarged portion) as shown in FIGS. 9 and 10. The openings can have any desired shape and/or size. In some embodiments, the inner diameter of the openings 21 is less than the inner diameter of the second port 20. With respect to the embodiments illustrated in FIGS. 9 and 10, passing insufflation gas through these openings into the body cavity is believed to provide for reduced tissue desiccation and increased local cooling by stimulating convection (e.g., reducing the "jet effect"). Alternatively, or additionally, this configuration can provide more efficient gas flow when surgical instruments are present in the cannula sleeve, e.g., by reducing interference with gas flow. The openings can be arranged along the sleeve in a variety of patterns and configurations. For example, the openings can be arranged along a portion of one side of the sleeve, or spirally along a portion of the length of the sleeve. The openings can be regularly or irregularly arranged along a portion of the length of the sleeve. Alternatively, or additionally, there can be opposing and/or non-opposing openings along a portion of the length of the sleeve.

In the embodiments shown in FIGS. 7 and 8, the cannula assembly 500 comprises a movable cover 110 communicating with the port(s), wherein moving the cover allows the gas flow rate through the port(s) to be adjusted. For example, the cover can include one or more openings that can be aligned with the opening(s) in the ports, or the cover can be moved to uncover the opening(s).

The cannula assembly can include a plurality of gas filters, e.g., gas filter 200A, 200B and 200C as shown in FIGS. 6A and 6C.

The gas filter 200 can have a variety of configurations, e.g., substantially planar (FIGS. 5, 6A, 6C, 11 and 12) or cylindrical (FIGS. 2–4, 10, and 13), or combinations thereof (not shown). If desired, the gas filter (in any configuration) can have an opening or hollow cavity allowing instrument passage therethrough, e.g., opening or cavity 250 as shown in FIGS. 2–4, 10, and 13. In some embodiments, the gas filter has at least one element in addition to hydrophobic retentive element 201, and in the embodiments illustrated in FIGS. 2–5, 11, and 13, the gas filter 200 further comprises prefilter element 202 and odor reducing element 203.

The gas filter 200 can be retained (and preferably, sealed) in the housing using a variety of techniques and/or structures. For example, FIGS. 2 and 10 show a gas filter sealing arrangement 300 comprising two o-rings.

Figure 2:
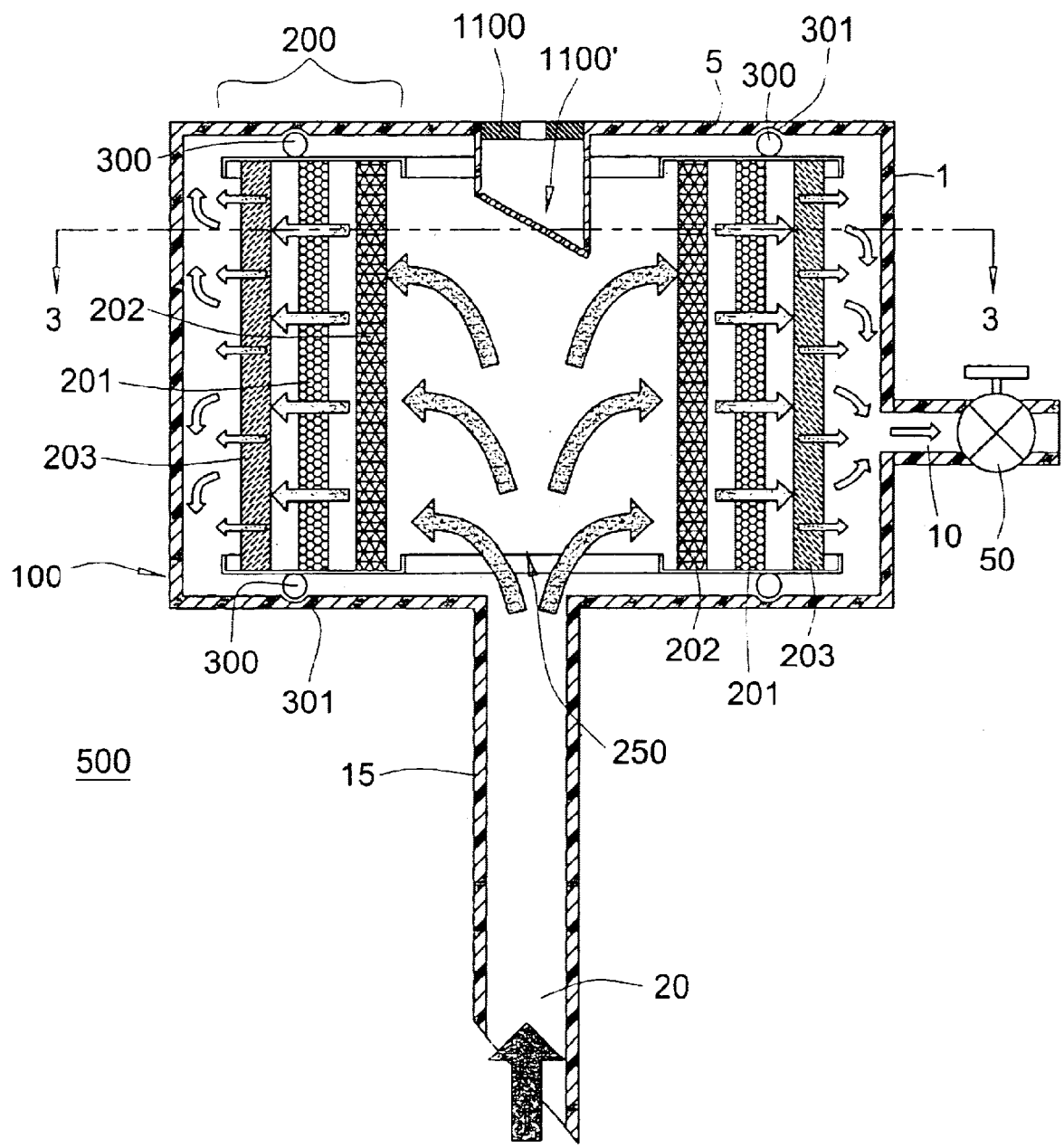
FIG. 2 is a side cross-sectional view of an embodiment of a cannula assembly including a cylindrical gas filter.

Utilizing the cannula assembly 500 illustrated in FIG. 2 for reference, and manipulating the flow control device 50 during insufflation and de-sufflation as appropriate, insufflation gas can be passed through the first port 10, through the gas filter 200, and through the second port 20 into the body cavity to inflate the cavity or replenish gas vented or de-sufflated from the cavity. During the treatment protocol, gas (typically smoke) can be vented or de-sufflated from the body cavity, e.g., to clear the surgeon's field of vision, by passing it from the cavity, through the second port, gas filter, and through the first port. Thus, undesirable material is removed from the gas entering the body cavity, and undesirable material is removed from gas exiting the body cavity.

The cannula and cannula assembly can be configured for use with surgical instruments wherein gas can be filtered while the instruments are being utilized. Typically, as shown in FIGS. 2, 5, 6, and 10–13 (cannula assembly) or FIG. 9 (cannula), embodiments of the invention include at least one instrument sealing arrangement 1100 that is arranged to contact the instrument(s) and to reduce or minimize the leakage of gas from the inflated body cavity into the atmosphere. Preferably, the sealing arrangement, or an additional sealing arrangement, is arranged to reduce or minimize the leakage of gas therethrough when no instrument is present. In accordance with these embodiments, the cannula and cannula assembly are configured to allow a surgical instrument (e.g., trocar 1000 shown in FIG. 1) to be removably passed through the second port, e.g., wherein the cannula sleeve comprises the second port. In an exemplary cannula or cannula assembly housing, the housing comprises a first portion, suitable for grasping while manipulating the surgical instrument or preparing to manipulate the instrument, attached to a second portion, comprising the cannula sleeve, wherein the first portion of the housing has a larger inner diameter than the second portion.

Illustratively, the top wall or cover of the cannula or cannula assembly (e.g., part of the first portion of the housing) is removed (e.g., top wall 5 shown in FIG. 1 is removed), opened, or accessed (preferably while at least substantially maintaining a gas-tight seal between the inflated body cavity and the external environment), and the surgical instrument is passed through the sleeve and second port into the body cavity (e.g., the pnuemoperitoneum), or the instrument is passed from the body cavity and through the cannula sleeve and second port. In some embodiments, the surgical instrument can be passed through the cannula or cannula assembly without removing a wall or cover, e.g., the top of the cannula or assembly includes an instrument sealing arrangement. Typically, in those embodiments wherein the wall or cover is not removed, the wall or cover includes an instrument sealing arrangement (e.g., sealing arrangement 1100 attached to top wall 5 shown in, for example, FIG. 2), comprising a gasket (e.g., a resilient gasket) that can be penetrated by an instrument and will seal against the exterior of the instrument. For example, the gasket can have an opening that is stretched larger when the instrument passes through it. In this illustrated embodiment, the cannula assembly also includes a second instrument sealing arrangement (1100') that will close off (e.g., via a movable flap) to reduce the undesired leakage of gas from the inflated body cavity into the atmosphere when an instrument is not present. Embodiments of the cannula assembly can include a single instrument sealing arrangement, or two or more sealing arrangements (that can be in contact with each other, or arranged separately in or on the housing).

In one example, using the embodiments of the cannula assembly 500 shown in FIG. 2 for reference, a surgical instrument such as a trocar is passed into the housing through a first sealing arrangement 1100, and a second sealing arrangement 1100'. The illustrated first sealing arrangement is arranged to provide for sealing against an instrument passing therethrough to reduce or minimize gas leakage between the instrument and the arrangement to maintain the inflation of the body cavity. FIG. 2 shows an embodiment wherein the instrument is to be passed through the gas filter, and the instrument passes through the hollow cavity 250 of the gas filter 200, through the port 20 of the cannula sleeve 15, and extends from the end of the sleeve. In those embodiments wherein the instrument is a trocar, the tip of the trocar (extending from the end of the sleeve) is used to puncture the wall 900 of the body cavity (shown in FIG. 1), and a portion of the cannula sleeve is passed into the body cavity. Subsequently, the trocar is withdrawn from the body cavity through the second port, and the interior of the cannula sleeve. Typically, the trocar is withdrawn through the second and first sealing arrangements and from the cannula or cannula arrangement. Preferably, the second instrument sealing arrangement 1100' automatically closes and/or seals once the trocar (or any other instrument) is withdrawn through the second sealing arrangement, e.g., so that gas leakage is minimized or reduced once the body cavity is inflated.

During the surgical protocol, one or more surgical instruments can be removably passed through the second port. Illustratively, after a trocar is removed from the cannula assembly, and the body cavity is inflated, a laser can be passed into the cavity (e.g., so that cutting can be carried out), and removed so that a camera can be passed through the port into the cavity. A plurality of cannula assemblies can be utilized, e.g., so that different instruments (for example, a laser and an optic probe) can be utilized at the same time. As noted above, at least one instrument sealing arrangement is typically arranged to provide for sealing against an instrument passing therethrough so gas leakage is reduced or minimized.

In those embodiments wherein a surgical instrument is removably passed through the second port of the cannula or cannula assembly, the second port typically has an inner diameter of about 1 mm or more, preferably, about 5 mm or more, and in some embodiments, the inner diameter can be in the range of from about 10 mm to about 12 mm, or more. Accordingly, in those embodiments wherein the gas filter has a hollow cavity allowing instrument passage therethrough, the inner diameter of the cavity is typically at least as large as that of the second port. More typically, the inner diameter of the cavity is larger than the inner diameter of the second port.

The housing 100 can be made from any suitable material as is known in the art. Exemplary materials include polymeric materials such as polycarbonate, acrylic, polypropylene, polystyrene, and polyethylene. Other suitable materials, particularly for those embodiments wherein the housing is reusable, include stainless steel (e.g., medical grade stainless steel).

The housing can have any suitable shape and size. For example, the enlarged portion of the housing can be substantially rectangular, square, circular, oval, or another shape. One or more side walls can be substantially planar and/or rounded. In some embodiments, e.g., wherein the gas filter has a substantially cylindrical configuration, the housing has a substantially continuous oval or circular side wall. If desired, at least one surface of the gas filter can contact the interior surface of at least one wall such as a side wall (e.g., the interior surface of side wall 2 as shown in FIG. 6A) and/or there can be a space between the filter and the interior surface of at least one wall (e.g., the interior surface of side wall 1 as shown in FIGS. 2–5).

As will be discussed in more detail below, the housing can include additional structures and elements, e.g., one or more structures for supporting, retaining and/or sealing one or more gas filters in the housing and/or for separating one gas fluid flow path from another. For example, the embodiment illustrated in FIGS. 6B, 6C, 11 and 12 show an assembly wherein the housing also includes an interior member 4 (e.g., an interior wall or a support such as, for example, a screen or mesh). The housing can include an interior wall wherein the interior wall includes a plurality of openings allowing gas passage therethrough. In some embodiments of the invention (e.g., with reference to FIGS. 6A–C, the housing can be configured (for example, with one or more interior walls and/or a sleeve including a port within a sleeve including another port) to separate one gas flow path from another. While the embodiment illustrated in FIG. 6C shows insufflation and de-sufflation gas flow paths for reference, it should be recognized that gas is not flowing along both types of flow paths simultaneously.

The housing 100, as well as the cannula 400 and cannula assembly 500, are sterilizable in accordance with a variety of protocols as are known in the art, e.g., autoclaving, and ethylene oxide treatment.

In some embodiments, one or more ports (e.g., ports 10 and 11) comprise fittings or connectors, such as luer connectors. Other connector configurations include, for example, push-on, barbed and clamped. Typically, at least one connector comprises a quick disconnect connector. In some preferred embodiments, wherein a portion of the side wall of the housing includes a port (e.g., the first port), the port further comprises a connector. However, in some other embodiments, e.g., wherein the port comprises two or more openings (e.g., ports 11 and 14 as shown in FIG. 6A), the port does not include a connector.

As noted above, the second port 20 typically has an inner diameter of about 1 mm or more, and preferably about 5 mm or more. In those embodiments wherein the first and/or third port (10, 11) comprises a single opening, a typical inner diameter is about 0.08 inches (about 0.2 cm) or more, more typically, about 0.2 inches (about 0.5 cm) or more, and in some embodiments, is in the range from about 0.25 inches to about 0.3 inches (about 0.64 cm to about 0.77 cm). In a preferred embodiment of the cannula assembly, the assembly is capable of allowing a gas flow rate through the first and/or third ports and the gas filter of at least about 10 L/min at 15 mm Hg, and can be capable of allowing a flow rate therethrough of at least about 15 L/min at that pressure.

In those embodiments wherein the first and/or third port includes a plurality of openings (e.g., as shown in FIGS. 6A and 7), when the openings are not restricted by a movable cover (e.g., cover 110 as shown in FIG. 7), and in those embodiments wherein the cannula sleeve has a plurality of openings (e.g., as shown in FIGS. 9 and 10), the assembly is preferably capable of allowing a gas flow rate through the port(s), the openings, and the filter, of at least about 10 L/min at 15 mm Hg, and can be capable of allowing a flow rate therethrough of at least about 15 L/min at that pressure.

The cannula and cannula assembly can include other structures and elements such as at least one flow control device, e.g., at least one of a clamp, valve and a movable plate. For example, FIGS. 1, 2, 5, 9 and 10 show a flow control device 50 comprising an adjustable valve (that can comprise, for example, a two-way or three-way valve). Additionally, or alternatively, a tubing set (not shown) that can be attached to the cannula or cannula assembly (e.g., by connection to the first port) can include one or more flow control devices. In some embodiments, particularly in some embodiments wherein the cannula or cannula assembly is only used to filter insufflation gas, the cannula or assembly does not include a flow control device or the flow control device is not used to control gas flow. In other embodiments, e.g., as shown in FIGS. 7 and 8 (gas filter not shown), the cannula assembly can include a movable plate 110 (typically including one or more openings) that allows fluid flow through the associated port(s) to be adjusted. For example, in a first position the plate 110 covers the openings in the first port 10 (FIG. 7) or covers the ports 10 and 11 (FIG. 8) and thus prevents fluid flow therethrough. The plate can be moved to a second position wherein the openings and ports are completely or partially uncovered, thus allowing fluid flow. If desired, the movement of the plate can be continuously adjusted (e.g., to vary the flow rate), or the plate can be moved to one or more predetermined positions, e.g., to allow predetermined flow rates. In one exemplary variation of the embodiment illustrated in FIG. 6, the assembly can include one or more movable plates for adjusting flow through ports 11 and 14.

As noted above, the gas filter 200, preferably a smoke filter, comprises at least one gas filter element (preferably at least one smoke filter element) comprising at least one porous retentive element, preferably a porous hydrophobic medium. FIGS. 2–5, 11, and 13 show gas filter 200 comprising hydrophobic retentive element 201. The gas filter element (e.g., hydrophobic retentive element 201) can be produced from any suitable natural and/or synthetic material capable of forming a substrate, fibers or a membrane that is compatible with the gas and smoke. In some embodiments, commercially available materials are preferred. Suitable polymers include, but are not limited to, polytetrafluoroethylene (PTFE), any nylon, e.g., 6, 6T, 11, 46, 66, and 610, polyvinylidene difluroride (PVDF), polyethersulfone (PES), polypropylene, polyester, as well as copolymers and/or combinations thereof.

Other suitable materials include cellulosic derivatives. Non-resinous materials, such as glass fibers, including microglass and/or laminated glass, can also be used.

Commercially available media, such as those available from Pall Corporation (East Hills, N.Y.) under the trademarks SUPOR®, VERSAPOR®, and PALLFLEX®, are also suitable. Other suitable commercially available media include, but are not limited to, H&V HOVOGLAS™ (Hollingsworth & Vose Company, East Walpole, Mass.) and VERIFLO™ (Enhanced Filter, Ventura, Calif.).

The gas filter element may remain untreated, or may be treated to increase its effectiveness. Surface characteristics of the element can be modified (e.g., to affect the CWST, to include a surface charge, e.g., a positive or negative charge and/or to alter the polarity or hydrophilicity of the surface) by chemical reaction including, for example, wet or dry oxidation, by coating or depositing a polymer on the surface, or by a grafting reaction. Modifications include, e.g., irradiation, a polar or charged monomer, coating and/or curing the surface with a charged polymer, and carrying out chemical modification to attach functional groups on the surface. Grafting reactions may be activated by exposure to an energy source such as gas plasma, heat, a Van der Graff generator, ultraviolet light, electron beam, or to various other forms of radiation, or by surface etching or deposition using a plasma treatment. The filter element can be initially hydrophilic, and treated to be made hydrophobic, and/or the filter element can be treated to increase its hydrophobicity (i.e., to make it more hydrophobic). Other treatments comprise, for example, modifying the element to include an antimicrobial agent to kill or inactivate undesirable materials such as viruses and/or bacteria in the gas or smoke as the gas passes through the element.

The gas filter, and any of the filter elements, can have a variety of configurations. The filter can include a plurality of elements having different configurations. For example, at least one element can be substantially planar, pleated, corrugated, cylindrical, cylindrical and pleated, while providing sufficient surface area available for filtration. Typically, the gas filter element (e.g., the hydrophobic retentive element) has an effective filtration area of at least about 9 $cm^2$ or more, more typically, at least about 12 $cm^2$ or more, preferably, at least about 15 $cm^2$ or more, and even more preferably, at least about 18 $cm^2$ or more. Embodiments of the gas filter have an effective filtration area of about 50 $cm^2$, or more. In some embodiments, e.g., wherein the gas filter element is intended for use for filtering vented or de-sufflation gas, the element has an effective filtration area of at least about 20 $cm^2$ or more.

As noted earlier, the gas filter can include additional components such as additional elements. For example, the gas filter can include one or more upstream and/or downstream elements, such as a prefilter element, an odor-reducing element, as well as support and/or drainage elements. The additional elements can be treated or modified and/or can have a variety of configurations and suitable effective filtration areas as described above for the gas filter element. In some embodiments, a gas filter element can have a different configuration than at least one of the other filter elements. For example, in the embodiment illustrated in FIG. 4, gas filter element 201 has a pleated configuration, and odor-reducing element 203 has a non-pleated configuration.

The gas filter can comprise a composite, e.g., wherein one or more components is secured, e.g., laminated, to the gas filter element. Alternatively, or additionally, the additional elements can be separate from the gas filter. If desired, the filter can be assembled to provide, for example, a cartridge or cassette.

Preferably, the gas filter also includes an odor-reducing element. The filter may also include a prefilter element, or the retentive member can provide retention and prefiltration (e.g., the retentive membrane can comprise a plurality of depth filter elements and/or fibrous layers). Typically, the prefilter element and odor-reducing element each comprise at least one porous medium.

In the illustrative embodiments shown in FIGS. 2–5, 6A, 6C, 11, and 13, the gas filter comprises a smoke filter, and the filter also includes an odor-reducing element 203, disposed downstream (with respect to venting or de-sufflation gas flow) of the hydrophobic retentive element 201. However, in another embodiment (not shown), the odor-reducing element is disposed upstream of the hydrophobic retentive element. In other embodiments (e.g., the embodiment of the gas filter 200C as shown in FIGS. 6B and 6C), the gas filter does not include an odor-reducing element.

The embodiments illustrated in FIGS. 2–5, 11 and 13 each include at least one prefilter element 202 and at least one odor-reducing element 203. Either of these elements can include a plurality of layers. Preferably, the prefilter element and the odor-reducing element are very open and have good porosity. The prefilter element and odor reducing element can comprise any suitable woven or non-woven material, and can be formed from natural and/or synthetic material, e.g., fibers, polymeric material and/or glass. Exemplary materials include polypropylene, polyester, polyethersulfone, carbon (preferably activated carbon, e.g., charcoal and/or novoloid fibers) and/or microglass. Carbon can be granular and embedded in a matrix, or fibers mixed in a blend (e.g., in a cotton/cellulose blend or cellulose blend).

In some embodiments including a separate prefilter element, the prefilter element comprises a fibrous medium, e.g., including polymeric fibers and/or glass fibers.

In some embodiments including an odor-reducing element 203, the odor-reducing element also reduces the passage therethrough of undesirable substances such as other chemical matter and/or organic vapors. For example, in one illustrative embodiment including an odor-reducing element, the element can reduce the passage therethrough at least one of benzene, formaldehyde, hydrogen cyanide, and toluene.

In one preferred embodiment, the odor-reducing element comprises a carbon medium, preferably an activated carbon medium, even more preferably an activated fibrous carbon medium. One example of a suitable commercially available medium is the activated charcoal ULTRASORB™ (Enhanced Filter, Ventura, Calif.), e.g., as a fibrous or granulated laminate. Another example of a suitable commercially available medium is AQF® media (AQF Technologies, Charlotte, N.C.), e.g., activated carbon in a three dimensional polyester non-woven structure.

Typically, as described above with respect to venting or de-sufflation gas flow, in those embodiments including an odor-reducing element, the odor-reducing element is downstream of the hydrophobic retentive member, i.e., during venting the gas passes through the retentive member before passing through the odor-reducing element. However, in other embodiments (involving venting, de-sufflation and/or insufflation applications), the odor-reducing element can be upstream of the hydrophobic retentive member, and can be the first element in the smoke filter.

The gas filter 200 can be retained (and preferably, sealed) in the housing using a variety of techniques and/or structures. Typically, the cannula assembly includes a gas filter sealing arrangement comprising at least one of a potting material, an adhesive, a solvent, a gasket (including, but not limited to an o-ring), and a weld (e.g., via radio frequency sealing, spin welding, ultrasonic sealing and/or heat sealing (including fusion welding)). The gas filter can be sealed in the housing using at least one of compression and snap fitting. In some embodiments wherein the cannula assembly includes a plurality of gas filters, different sealing arrangements can be used for the different filters. The illustrative examples shown in FIGS. 2 and 9 show embodiments of a gas filter sealing arrangement 300 comprising two o-rings (FIG. 2 also shows depressions or grooves 301 wherein the o-rings fit in the depressions and are compressed to provide a seal).

In some embodiments wherein the housing is re-usable, the sealing arrangement is preferably configured (typically as a cartridge or cassette) for ease in removing and replacing the gas filter. For example, the cannula assembly can be used in a surgical protocol, and the housing is subsequently opened and the gas filter is removed and discarded. The housing is sterilized, and a replacement filter is inserted therein. The cannula assembly is subsequently sterilized, and used in another surgical protocol. If desired, the housing and the sealing arrangement can be configured for a variety of gas filters and applications. For example, the same housing can be configured for use with different gas filters, e.g., the first replacement filter is suitable for filtering insufflation gas, the second replacement filter is suitable for filtering de-sufflation gas. Alternatively, or additionally, replacement filters can be suitable for filtering insufflation and de-sufflation gas, or a replacement filter set can include an insufflation filter and a de-sufflation filter (e.g., wherein the housing includes at least three ports and provides at different gas flow paths for the different gases).

In some embodiments, the gas filter also includes one or more window elements, e.g., window elements 330 as shown in FIG. 11. In a typical embodiment, at least one window element provides surface area for securing elements of the gas filter together and/or for securing the filter to the housing. For example, in the embodiment illustrated in FIG. 11, window elements secured to the smoke filter element 201, and the prefilter element 202, allow these elements to be sealed together.

One or more window elements can have one or more windows or openings, e.g., areas wherein the upstream and/or downstream surfaces of the gas filter are exposed to gas flow.

The window elements and windows can be of any suitable number, size and/or shape (e.g., rectangular, circular, triangular, oval). The gas filter can include a plurality of window elements having different characteristics (e.g., shape, size and/or number of windows), and a window element can have a plurality of windows of different characteristics.

The widow elements can be secured to, for example, either of the opposing surfaces of a gas filter element or a prefilter element. Securing, e.g., sealing, can include, for example, utilizing an adhesive, a solvent, radio frequency sealing, ultrasonic sealing and/or heat sealing. In some embodiments, e.g., some embodiments providing a subcomponent or subassembly of the filter device including carbon media, radio frequency sealing may be less desirable.

Typical materials suitable for producing the window element(s) include, but are not limited to, for example, plasticized polyvinyl chloride (PVC), polyester, polyurethane, polycarbonate, polypropylene, polyolefin, polyethylene, ethylene vinyl acetate (EVA), and combinations of materials.

All of the references cited herein, including publications, patents, and patent applications, are hereby incorporated in their entireties by reference.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. A cannula assembly comprising:
a housing comprising at least a first port and a cannula sleeve, the cannula sleeve comprising a second port, wherein said housing defines a fluid flow path between the first port and the second port, and said housing is arranged to allow a trocar to be removably passed through the second port; and
a cylindrical gas filter disposed in the housing, across the fluid flow path, wherein said gas filter comprises at least one gas filter element comprising at least one porous medium, and the gas filter has an opening allowing the trocar to be removably passed through the opening while the cannula assembly extends into a patient's body cavity.

2. The assembly of claim 1, wherein the gas filter comprises a cylindrical pleated filter.

3. The assembly of claim 2, wherein the filter has an effective filtration area of at least about 9 $cm^2$.

4. The assembly of claim 1, wherein the housing has at least one side wall having an exterior surface and an interior surface, and the gas filter has a first surface and a second surface, and the first surface of the gas filter contacts the interior surface of the side wall.

5. The assembly of claim 1, wherein the housing has at least on side wall having an exterior surface and an interior surface, and the gas filter has a first surface and a second surface, and the first surface of the gas filter is spaced from the interior surface of the side wall.

6. The assembly of claim 1, wherein the filter has an effective filtration area of at least about 9 $cm^2$.

7. The assembly of claim 1, wherein the first port has a diameter of at least about 0.08 inches (about 0.2 cm).

8. The assembly of claim 7, wherein the first port has a diameter of at least about 0.2 inches (about 0.5 cm).

9. The assembly of claim 1, wherein the first port comprises two or more openings.

10. The assembly of claim 9, wherein the housing includes at least one side wall including the first port comprising two or more openings.

11. The assembly of claim 1, further comprising a cover movable from a first position to a second position, wherein the first position allows gas flow through the first port, and the second position prevents gas flow through the second port.

12. The assembly of claim 11, wherein the cover is adjustable between the first position and the second position.

13. The assembly of claim 11, wherein the housing includes the cover.

14. The assembly of claim 1, wherein the sleeve includes two or more openings along the length of the sleeve.

15. The assembly of claim 1, wherein the filter element comprises a hydrophobic membrane.

16. The assembly of claim 1, wherein the second port has an inner diameter of at least about 5 mm.

17. A method for filtering gas comprising:
passing at least one gas through the cannula assembly of claim 1.

18. The method of claim 17, comprising passing a de-sufflation gas through the cannula assembly.

19. The method of claim 17, further comprising passing a surgical instrument through the gas filter opening and through the second port of the cannula assembly.

20. The method of claim 17, comprising passing an insufflation gas through the cannula assembly.

21. A method for treating gas comprising passing the gas through the cannula assembly of claim 9, wherein gas passes through the two or more openings.

22. A method for treating gas comprising passing the gas through the cannula assembly of claim 14, wherein gas passes through the two or more openings.

23. A method for filtering gas comprising passing a gas through a first port of a housing, through a gas filter in the housing to provide a filtered gas, wherein the gas filter has an opening allowing a trocar to be removably passed therethrough, passing the filtered gas through a second port of the housing, and into a patient's abdominal cavity.

24. A cannula assembly comprising:
a housing comprising at least a first port and a cannula sleeve, the cannula sleeve comprising a second port, wherein said housing defines a fluid flow path between the first port and the second port, and said housing is arranged to allow a surgical instrument comprising at least one of a trocar, laparoscope, optic probe, scalpel, laser, ultrasonic device, electrocautery device, and camera, to be removably passed through the second port; and
a cylindrical gas filter disposed in the housing, across the fluid flow path, wherein said gas filter comprises at least one gas filter element comprising at least one porous medium, and the gas filter has an opening allowing the surgical instrument to be removably passed through the opening while the cannula assembly extends into a patient's body cavity.

25. A method for filtering gas comprising
obtaining a cannula assembly comprising a housing comprising at least a first port and a cannula sleeve, the cannula sleeve comprising a second port, wherein said housing defines a fluid flow path between the first port and the second port, and said housing is arranged to allow a trocar to be removably passed through the second port; and a cylindrical gas filter disposed in the housing, across the fluid flow path, wherein said gas filter comprises at least one gas filter element comprising at least one porous medium, and the gas filter has an opening allowing the trocar to be removably passed through the opening;
passing a gas through the first port of the housing, through the gas filter in the housing to provide a filtered gas, passing the filtered gas through the second port of the housing, and into a patient's abdominal cavity.

26. A method for filtering gas comprising
obtaining a cannula assembly comprising a housing comprising at least a first port and a cannula sleeve, the cannula sleeve comprising a second port, wherein said housing defines a fluid flow path between the first port and the second port, and said housing is arranged to allow a trocar to be removably passed through the second port; and a cylindrical gas filter disposed in the housing, across the fluid flow path, wherein said gas filter comprises at least one gas filter element comprising at least one porous medium, and the gas filter has an opening allowing the trocar to be removably passed through the opening;
passing a gas from a patient's abdominal cavity, through the second port of the housing, through the gas filter in the housing to provide a filtered gas, and passing the filtered gas through a first port of the housing.

27. The method of claim 26, wherein the gas includes smoke, and the filtered gas is depleted of smoke.

* * * * *